United States Patent [19]
Holt

[11] Patent Number: 5,787,894
[45] Date of Patent: Aug. 4, 1998

[54] JAW-CLOSING ANTI-SNORING SYSTEM

[76] Inventor: Harold Holt, 1706 Hackney, Houston, Tex. 77023

[21] Appl. No.: 764,069

[22] Filed: Nov. 6, 1996

[51] Int. Cl.$^6$ ........................................................ A61F 5/56
[52] U.S. Cl. ........................................... 128/848; 602/902
[58] Field of Search ................................. 128/846, 848, 128/857, 858; 602/17, 902

[56] References Cited

U.S. PATENT DOCUMENTS

| | | | |
|---|---|---|---|
| 649,896 | 5/1900 | Baughman | 128/848 |
| 1,216,679 | 2/1917 | Foster | 128/848 |
| 1,296,946 | 3/1919 | Galiardo | 128/848 |
| 2,999,232 | 9/1961 | Wilson | 128/848 |
| 4,366,815 | 1/1983 | Broomes | 128/848 |

Primary Examiner—Michael A. Brown

[57] ABSTRACT

A new Jaw-Closing Anti-Snoring System for controlling a user's snoring by supporting the user's jaw in a closed position while sleeping. The inventive device includes a strap having a first end and a second end, a securing means at the first and second end allowing the first end to removably secure to the second end, and an arcuate jaw support member formed to the shape of a jaw secured to the concentric portion of the strap and supporting the jaw of the user.

4 Claims, 3 Drawing Sheets

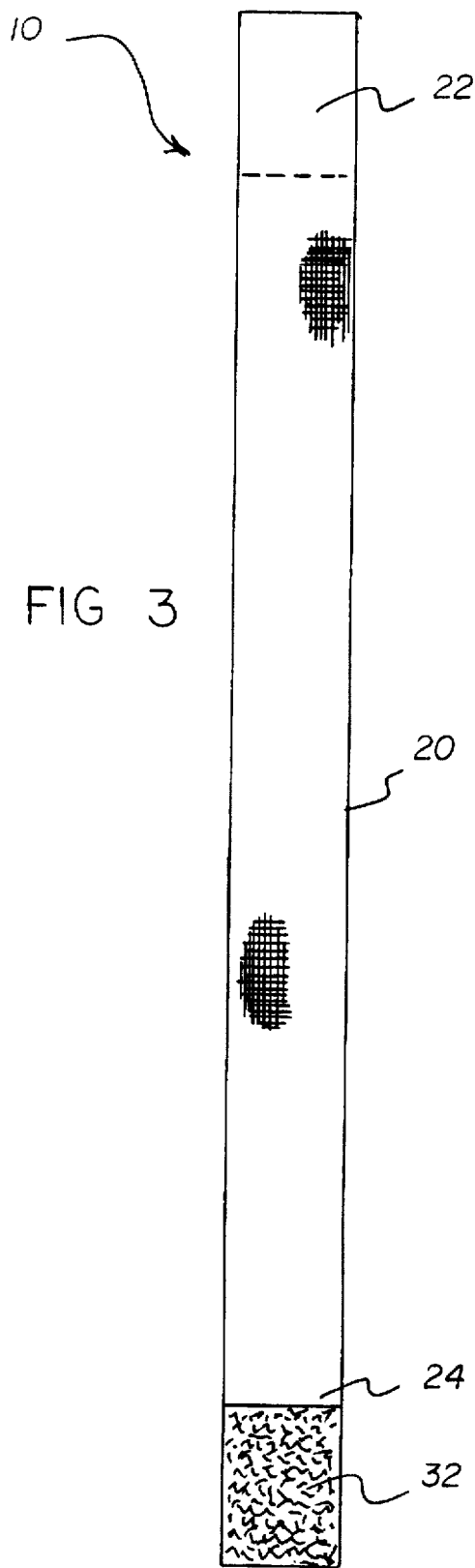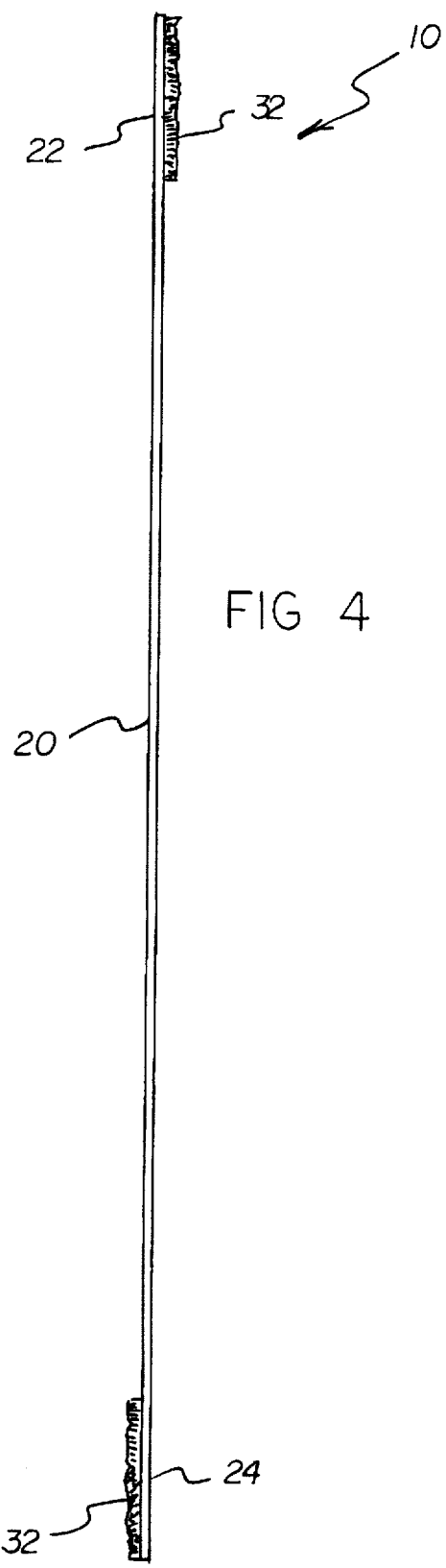

JAW-CLOSING ANTI-SNORING SYSTEM

BACKGROUND OF THE INVENTION

1. Related Data

The subject matter of the present utility patent application has been registered with the United States Patent and Trademark Office under the disclosure document program. The request was filed in the U.S. Patent and Trademark Office on Mar. 22, 1996 and was assigned the registration number 392,249.

2. Field of the Invention

The present invention relates to Anti-Snoring Devices and more particularly pertains to a new Jaw-Closing Anti-Snoring System for controlling a user's snoring by supporting the user's jaw in a closed position while sleeping.

DESCRIPTION OF THE PRIOR ART

The use of Anti-Snoring Devices is known in the prior art. More specifically, Anti-Snoring Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Anti-Snoring Devices include U.S. Pat. No. 4,366,815; U.S. Pat. No. 4,966,136; U.S. Design Pat. No. 251,682; U.S. Pat. No. 5,289,829; U.S. Pat. No. 4,719,876 and U.S. Pat. No. 5,383,475.

While these devices fulfill their respective, particular objectives and requirements, the aforementioned patents do not disclose a new Jaw-Closing Anti-Snoring System. The inventive device includes a strap having a first end and a second end, a securing means at the first and second end allowing the first end to removably secure to the second end, and an arcuate jaw support member formed to the shape of a jaw secured to the concentric portion of the strap and supporting the jaw of the user.

In these respects, the Jaw-Closing Anti-Snoring System according to the present invention substantially departs from the conventional concepts and designs of the prior art, and in so doing provides an apparatus primarily developed for the purpose of controlling a user's snoring by supporting the user's jaw in a closed position while sleeping.

SUMMARY OF THE INVENTION

In view of the foregoing disadvantages inherent in the known types of Anti-Snoring Devices now present in the prior art, the present invention provides a new Jaw-Closing Anti-Snoring System construction wherein the same can be utilized for controlling a user's snoring by supporting the user's jaw in a closed position while sleeping.

The general purpose of the present invention, which will be described subsequently in greater detail, is to provide a new Jaw-Closing Anti-Snoring System apparatus and method which has many of the advantages of the Anti-Snoring Devices mentioned heretofore and many novel features that result in a new Jaw-Closing Anti-Snoring System which is not anticipated, rendered obvious, suggested, or even implied by any of the prior art Anti-Snoring Devices, either alone or in any combination thereof.

To attain this, the present invention generally comprises a strap having a first end and a second end, a securing means at the first and second end allowing the first end to removably secure to the second end, and an arcuate jaw support member formed to the shape of a jaw secured to the concentric portion of the strap and supporting the jaw of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Jaw-Closing Anti-Snoring System apparatus and method which has many of the advantages of the Anti-Snoring Devices mentioned heretofore and many novel features that result in a new Jaw-Closing Anti-Snoring System which is not anticipated, rendered obvious, suggested, or even implied by any of the prior art Anti-Snoring Devices, either alone or in any combination thereof.

It is another object of the present invention to provide a new Jaw-Closing Anti-Snoring System which may be easily and efficiently manufactured and marketed.

It is a further object of the present invention to provide a new Jaw-Closing Anti-Snoring System which is of a durable and reliable construction.

An even further object of the present invention is to provide a new Jaw-Closing Anti-Snoring System which is susceptible of a low cost of manufacture with regard to both materials and labor, and which accordingly is then susceptible of low prices of sale to the consuming public, thereby making such Jaw-Closing Anti-Snoring System economically available to the buying public.

Still yet another object of the present invention is to provide a new Jaw-Closing Anti-Snoring System which provides in the apparatuses and methods of the prior art some of the advantages thereof, while simultaneously overcoming some of the disadvantages normally associated therewith.

Still another object of the present invention is to provide a new Jaw-Closing Anti-Snoring System for controlling a user's snoring by supporting the user's jaw in a closed position while sleeping.

Yet another object of the present invention is to provide a new Jaw-Closing Anti-Snoring System which includes a strap having a first end and a second end, a securing means at the first and second end allowing the first end to removably secure to the second end, and an arcuate jaw support member formed to the shape of a jaw secured to the concentric portion of the strap and supporting the jaw of the user.

Still yet another object of the present invention is to provide a new Jaw-Closing Anti-Snoring System that supports the user's jaw thereby eliminating snoring during sleep.

Even still another object of the present invention is to provide a new Jaw-Closing Anti-Snoring System that provides peace and quite for the user's loved ones by eliminating the snoring of the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a top view of the present invention in the unsecured position.

FIG. 4 is a side view of the present invention in the unsecured position.

DESCRIPTION OF THE PREFERRED EMBODIMENT

Figure 1:
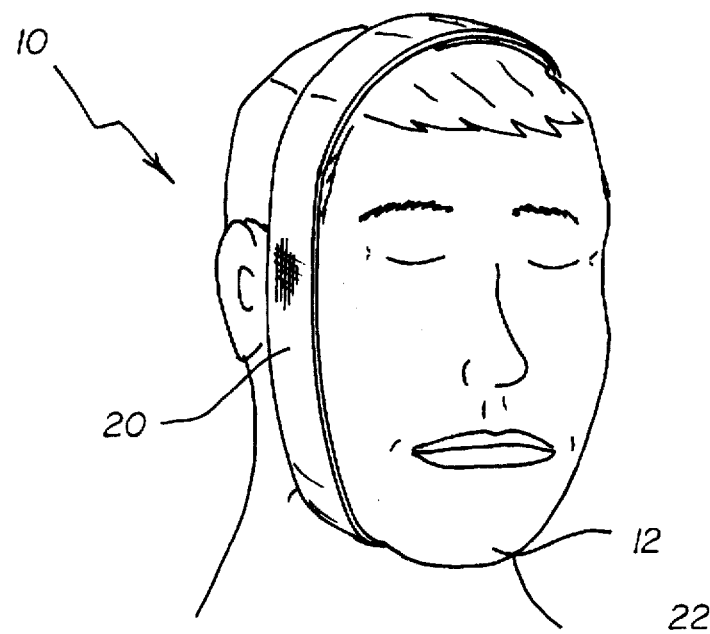
FIG. 1 is an upper side perspective view of a new Jaw-Closing Anti-Snoring System according to the present invention.
Figure 2:
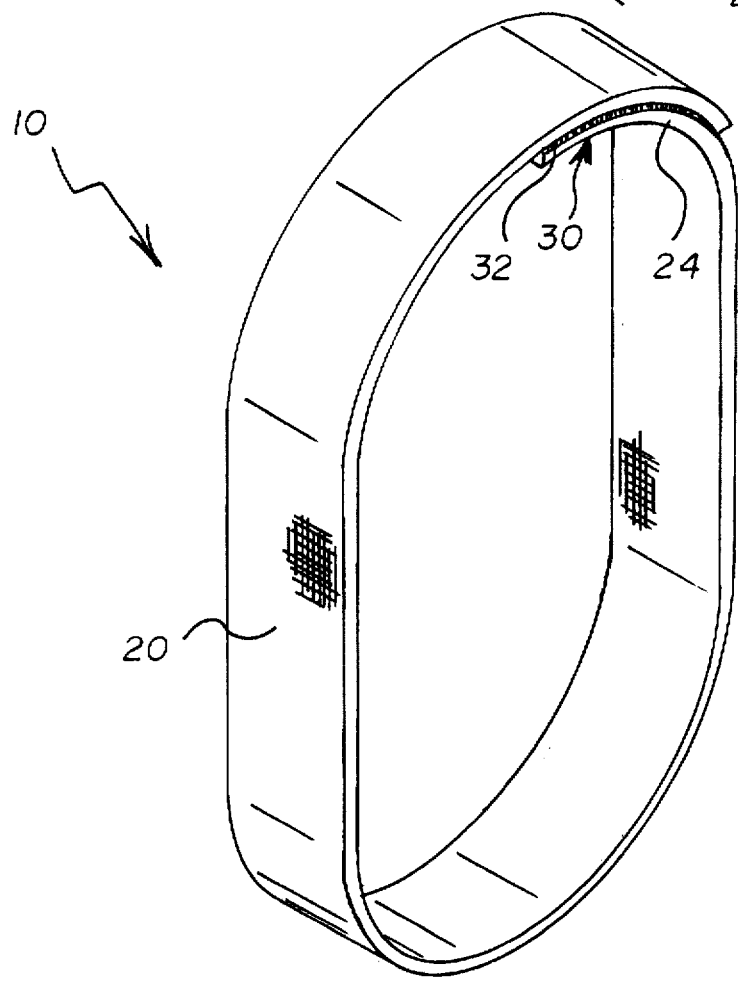
FIG. 2 is an upper side perspective view of the present invention.

With reference now to the drawings, and in particular to FIGS. 1 through 6 thereof, a new Jaw-Closing Anti-Snoring System embodying the principles and concepts of the present invention and generally designated by the reference numeral 10 will be described.

More specifically, it will be noted that the Jaw-Closing Anti-Snoring System 10 comprises a strap 20 having a first end 22 and a second end 24, where the concentric portion of the strap 20 is juxtaposed and supporting a jaw of the user, and a securing means 30 attached to the first end 22 and the second end 24, allowing the first end 22 to be removably secured to the second end 24 thereby retaining the strap 20 juxtaposed to and supporting the jaw of the user.

The strap 20 preferably is constructed from an elastic material thereby allowing opening of the jaw by the user when desired, while preventing unintentional opening of the jaw during sleep. The securing means 30 is also preferably constructed from Velcro 32 as best illustrated in FIGS. 3 and 4 of the drawings.

Figure 5:
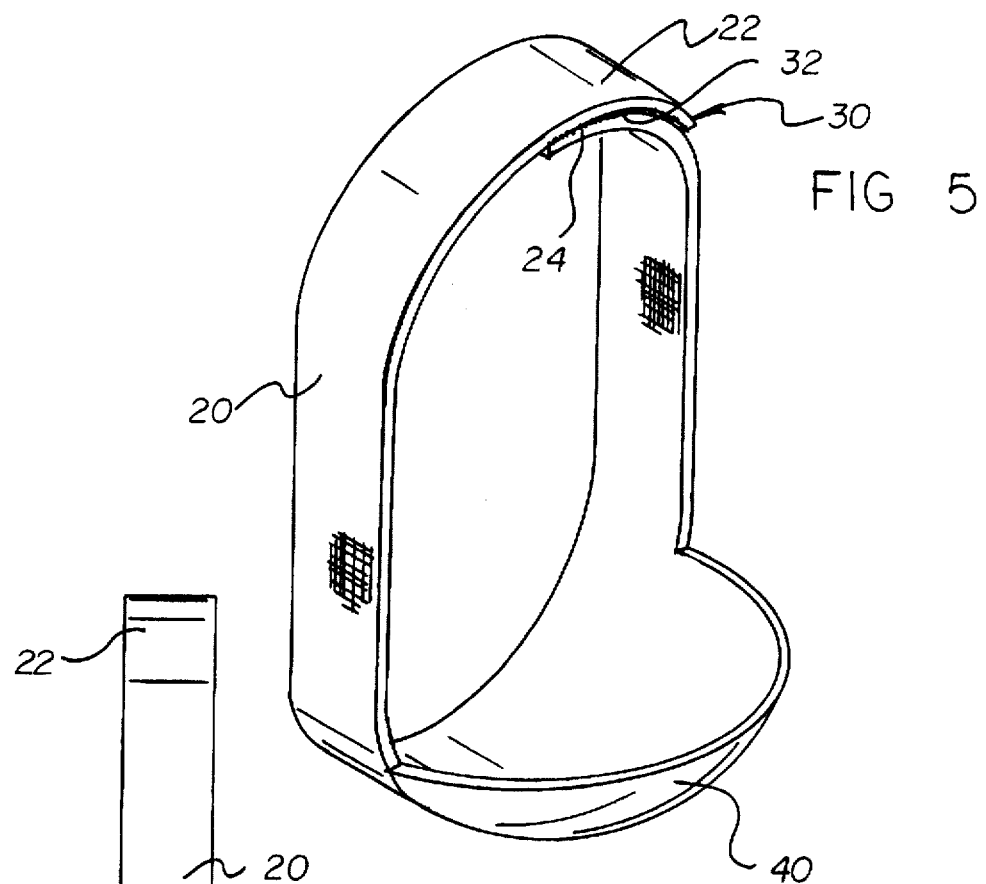
FIG. 5 is an upper perspective view of an alternative embodiment having an arcuate jaw support member.
Figure 6:
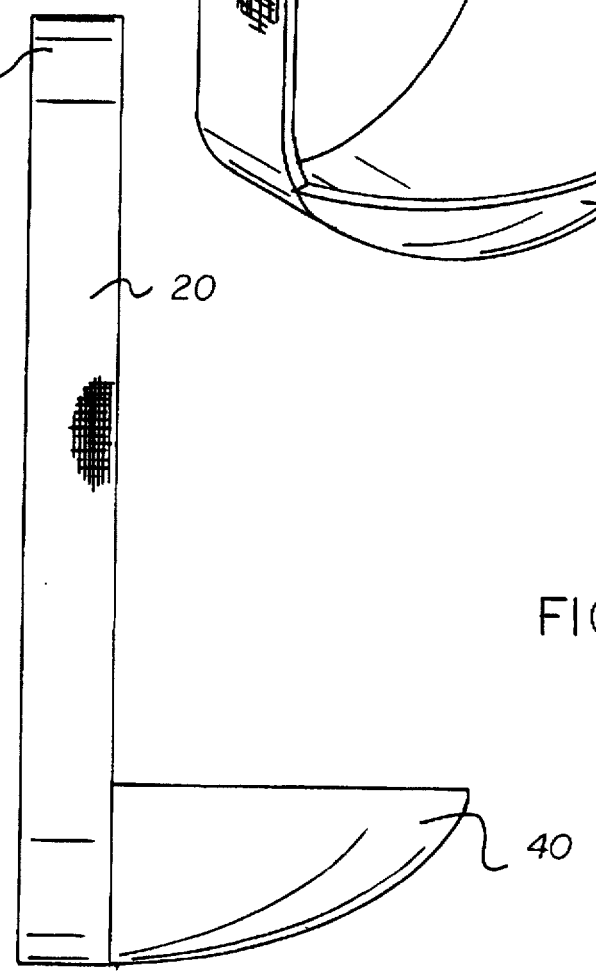
FIG. 6 is a side view of the alternative embodiment.

An alternative embodiment is illustrated in FIGS. 5 and 6, where it can be shown that the an arcuate jaw support member 40 is secured to the concentric portion of the strap 20. The support member 40 is preferably formed to the shape of the jaw of the user. The arcuate jaw support member 40 preferably is constructed from a resilient material.

In use, the user surrounds his or her head with the strap 20 with the concentric portion of the strap 20 juxtaposed to the bottom of the jaw 12 of the user as shown in FIG. 1 of the drawings. The user then secures the first end 22 to the second end 24 thereby retaining the concentric portion of the strap 20 juxtaposed to and supporting the jaw 12 of the user. The strap 20 thereby prevents unintentional opening of the jaw 12 during sleep, thereby preventing snoring of the user. In the alternative embodiment, the arcuate jaw support member 40 is juxtaposed to and supporting the jaw 12 of the user instead of the concentric portion of the strap 20. This provides increased stability of the present invention.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A jaw-closing anti-snoring system comprising:
    an elongate strap having a first end and a second end, said elongate strap having a first end portion, a second end portion and a central jaw support portion between said first and second end portions; and
    a securing means attached to said first end and said second end for removably securing said first end to said second end to retain said elongate strap about a user's head; said central jaw support portion being a continuous and concavely shaped cup for receiving the jaw of a user;
    wherein said elongate strap is bounded by spaced edges, one said edge being substantially straight, the other said edge having sections along said first and second end portions being substantially straight and equidistant from said one edge, the section of said other edge along said central jaw support portion extending substantially perpendicular to the sections of said other edge along said end portions and being arcuate between said end portions.

2. The jaw-closing anti-snoring system of claim 1 wherein said strap comprises a resiliently elastic material permitting longitudinal stretching of said strap to thereby permit intentional opening of said jaw by the user against the resistance of the strap while preventing unintentional opening of the jaw of said user during sleep.

3. The jaw-closing anti-snoring system of claim 1 wherein said securing means comprises hook and loop fastening means.

4. A jaw closing anti-snoring system comprising:

an elongate strap having a first end and a second end, said elongate strap having a first end portion, a second end portion and a central jaw support portion between said first and second end portions; and a securing means attached to said first end and said second end for removably securing said first end to said second end to retain said elongate strap about a user's head;

said central jaw support portion being a continuous and concavely shaped cup for receiving the jaw of a user;

wherein said strap comprises a resiliently elastic material permitting longitudinal stretching of said strap to thereby permit intentional opening of said jaw by the user against the resistance of the strap while preventing unintentional opening of the jaw of said user during sleep;

wherein said securing means comprises hook and loop fastening means;

wherein said elongate strap is bounded by spaced edges, one said edge being substantially straight, the other said edge having sections along said first and second end portions being substantially straight and equidistant from said one edge, the section of said other edge along said central jaw support portion extending substantially perpendicular to the sections of said other edge along said end portions and being arcuate between said end portions.

* * * * *